United States Patent [19]
Schmidt

[11] Patent Number: 5,496,373
[45] Date of Patent: Mar. 5, 1996

[54] ARTIFICIAL BONE REPLACEMENT FOR CADAVERS

[76] Inventor: Roderic H. Schmidt, 2544 Swan Blvd., Milwaukee, Wis. 53226

[21] Appl. No.: 227,684

[22] Filed: Apr. 14, 1994

Related U.S. Application Data

[63] Continuation of Ser. No. 947,685, Sep. 21, 1992, abandoned.

[51] Int. Cl.$^6$ .................................................. A61F 2/28
[52] U.S. Cl. ........................................ 623/16; 623/66
[58] Field of Search ..................... 623/16, 18; 403/108, 403/109, 377, 378, 379; 606/61

[56] References Cited

U.S. PATENT DOCUMENTS

| | | | |
|---|---|---|---|
| 2,600,578 | 6/1952 | Royer | 403/108 |
| 3,017,183 | 1/1962 | Chalcroft | 403/108 |
| 3,556,093 | 1/1971 | Quick | 128/137 |
| 4,505,268 | 3/1985 | Sgandurra | 606/61 |
| 4,863,473 | 9/1989 | Glowczewskie, Jr. et al. | 623/16 |

*Primary Examiner*—Debra S. Brittingham
*Attorney, Agent, or Firm*—Andrus, Sceales, Starke & Sawall

[57] ABSTRACT

A bone replacement structure for cadavers which includes telescoping tubes which are joined to each other with a stepped coupling. The coupling includes a first member with a series of spaced openings or holes and a second member having at least one end opening larger than the diameter of the spaced openings or holes. The members are joined by a plastic covered wire which is inserted with a press fit through the small openings to firmly and fixedly interconnect the extended members in position. The outer ends of the bone replacement tubes have a hangscrew unit which is separately secured to the tube end. Each hangscrew unit includes a short cup-shaped cap which telescopes over the end of the elongated tubular member. Prior to attachment of the cap, a hangscrew is clamped to the face of the cap by an internal nut and an external nut on the threaded rod to firmly fix the hangscrew to the member with the self-tapping screw projecting therefrom. The cap is then secured to the telescoping member, as by a suitable adhesive or the like. For a shoulder or hip connection, the cap is secured to an elbow having a leg press-fitted to the bone tube for proper bone placement. At least one turn of the thread of the rod is exposed externally beyond the exterior clamping nut.

10 Claims, 2 Drawing Sheets

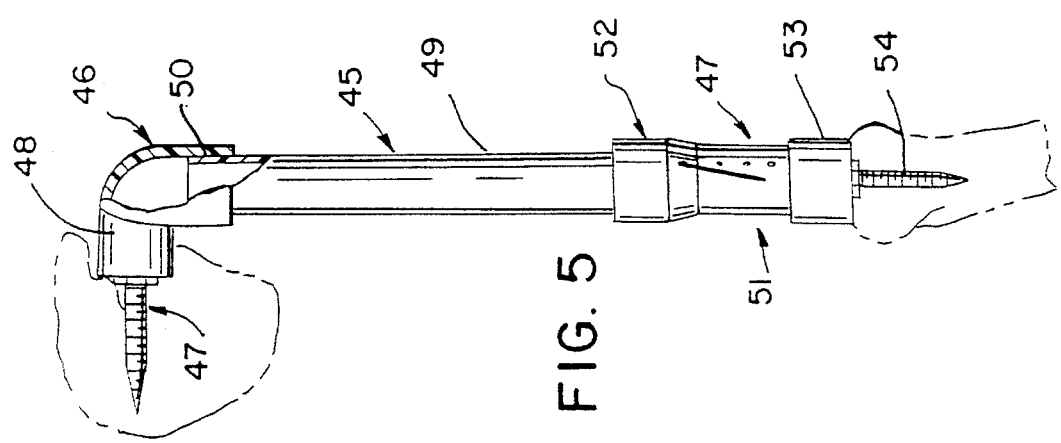
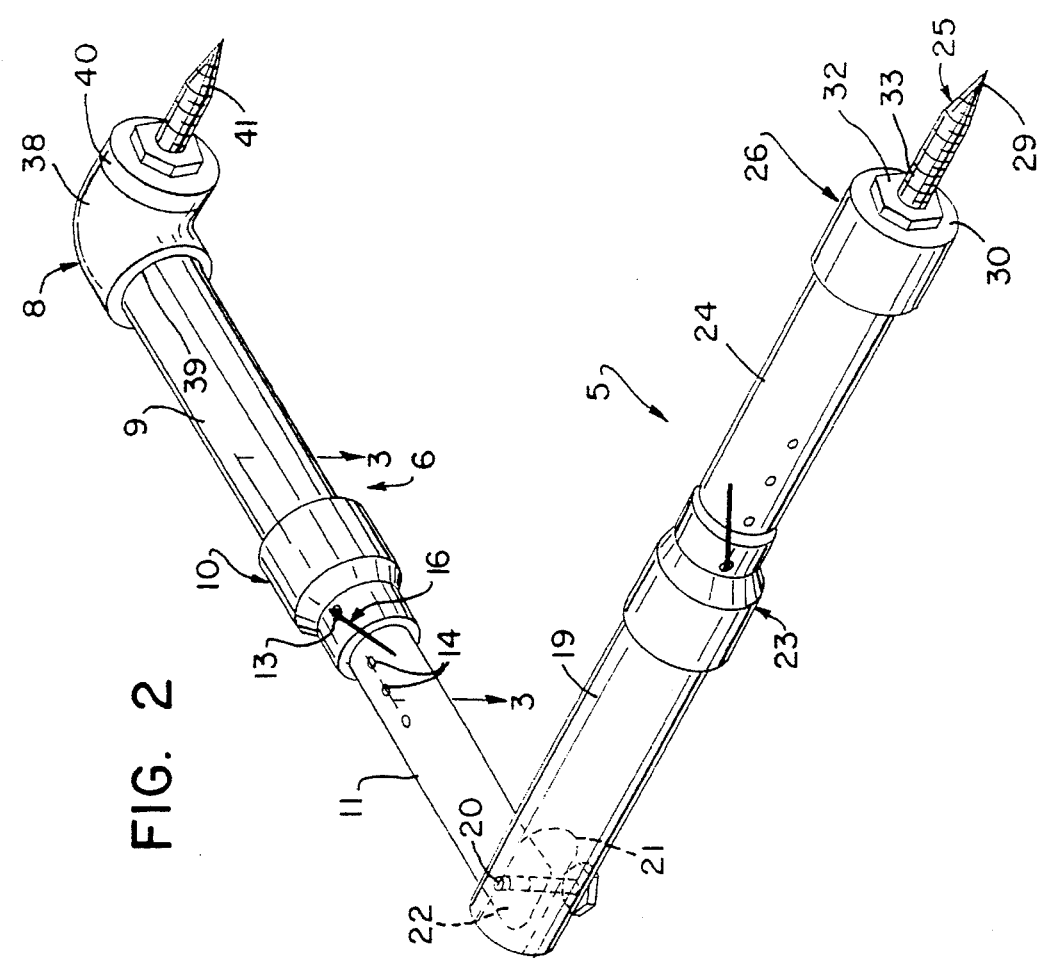

ARTIFICIAL BONE REPLACEMENT FOR CADAVERS

This application is a continuation of Ser. No. 07/947,685, filed Sep. 21, 1992, now abandoned.

BACKGROUND OF THE PRESENT INVENTION

This invention relates to an artificial bone replacement apparatus for a cadaver for purposes of presenting the deceased at a wake or the like.

Historically, deceased individuals are presented at a wake with the cadaver appropriately processed by an undertaker, and arranged in a display casket or the like. Bone reconstruction may be required and at times replacement of bone structure may be necessary. In addition, with modern day surgical procedures, bone transplants are made from the body of deceased donors, with immediate harvesting of the bone at donor's death. If an appropriate artificial bone replacement is not made, the body may have a distorted or unreal appearance as a result of the removal of the bone structures. Funeral directors for many years have used various rigid members such as a broom stick and the like to replace elongated bone structures.

Currently, commercial devices such as shown in U.S. Pat. No. 4,863,473 which issued Sep. 5, 1989 and U.S. Pat. No. 4,852,554 which issued Aug. 1, 1989 are available for replacing of various elongated bone structures. Generally, the prior art devices include telescoped and interconnected rigid tubular elements which permit elongation to the length of a removed bone structure, with screws secured to the opposite ends of the elements for direct attachment to the remaining bone structure of the deceased. U.S. Pat. No. 4,852,554 further discloses provision for construction of a simple hinge connection between telescopic sections which can be used for replacement of a bone structure including a pivoting interconnection such as an elbow, a knee or the like.

In coupling of the replacement unit to the remaining bone structure, the user pounds the tip of the attachment screw into the remaining bone and turns the screw into the bone. The force of pounding on the unit tends to loosen the attachment screw, and may make it difficult, if not impossible, to appropriately attach the element to the bone.

Further, interconnection of the telescoping tubular members has included collapsible interconnecting members such as encircling clamps, bolt and nut elements or the like. To provide for optimum appearance after bone replacement, the telescoping member and structure should be maintained at a minimum diameter or thickness in order to allow effective replacement of the tissue and skin about the replacement structure. Thus, if the replacement structure including the clamping elements is too large relative to the original bone structure, it is difficult to cover the replacement structure with the tissue and skin without creating an unnatural appearance.

There is therefore a need for a simple, reliable and effective telescopic bone replacement apparatus and system which maintains minimal cost, ease of use and assembly as well as reliability of placement and the like.

SUMMARY OF THE PRESENT INVENTION

The present invention is particularly directed to a new bone replacement structure for cadavers and the like which provides for reliable implantment to the remaining bone structure of the cadaver as well as minimizing problems of covering the replacement structure with the tissue and skin of the cadaver. Generally, in accordance with the teaching of the present invention, the telescoping structure is formed using minimum sized tubular components such as plastic tubes as bone members which are joined to each other with suitable stepped couplings. The telescoping components include a first member with a series of spaced openings and a second member having at least one end opening. With the holes aligned, the members are joined to lock the members against extension and further to limit rotation of the two members. In the preferred and unique structure, the members are joined by a simple rod or wire-like element, especially such as a plastic covered wire, which is inserted with a press fit through the openings to firmly and fixedly interconnect the extended members in position. When using a wire-like elements, the ends may be bent over into abutment with the plastic bone members.

In another unique feature of the teaching of this invention, each end of the bone replacement structure is provided with a special hangscrew which is separately secured to the end of the structure by a coupling unit. The coupling unit in a preferred structure is relatively a short cup-shaped member which telescopes over the end of the elongated tubular member. Prior to attachment of the cap unit member, a hangscrew is clamped to the face of the cap by an internal nut and an external nut to firmly fix the hangscrew to the member. The cup-shaped member is then secured to the telescoping member, as by a suitable adhesive or the like. In a particular commercial embodiment, at least one turn of the screw thread is exposed externally beyond the exterior clamping nut. The self-tapping screw portion of the hangscrew projects outwardly from the nut for interconnection of the screw portion to the bone structure. Applicant has found that the captured self-tapping screw provides a positive interconnection of the screw to the bone replacement structure and avoids the problem created when the element is forced into the bone structure for subsequent turning of the self-tapping screw into the bone structure.

The structure of the invention can be formed of readily available plastic tubing and coupling such as in various fluid and liquid flow systems. The present invention has been found to provide a significant improvement in the structures and acceptance by the trade.

BRIEF DESCRIPTION OF THE DRAWINGS

The drawings furnished herewith generally illustrate the best mode presently contemplated for carrying out the invention and are described hereinafter.

In the drawings:

FIG. 2 is a pictorial view of a bone replacement unit constructed in accordance with the teaching of the present invention and illustrating the implanting structure of the device;

FIG. 5 is a view illustrating a modification of the unit shown in FIGS. 1 and 2.

DESCRIPTION OF THE ILLUSTRATED EMBODIMENT

Figure 1:
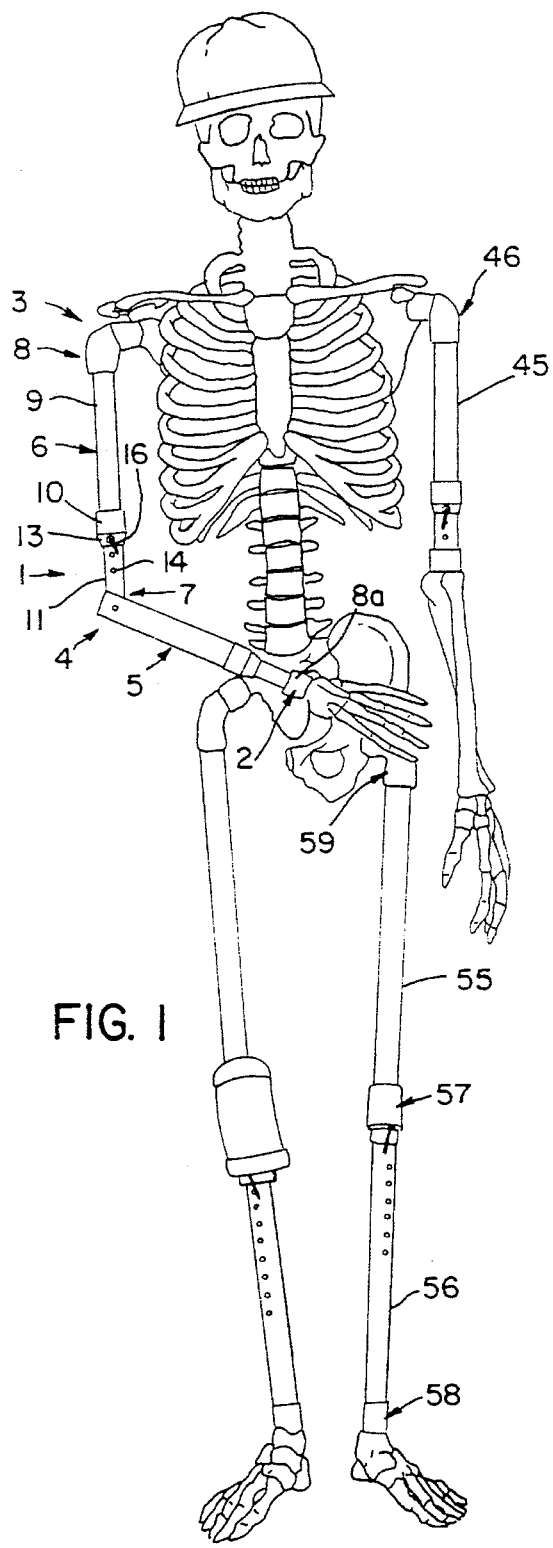
FIG. 1 is a simplified illustration of a cadaver showing the bone replacement structure in accordance with the teaching of the present invention.

Referring to the drawings and particularly to FIGS. 1 and 2, bone replacement devices are illustrated which may be used to replace the various limbs including the arms and legs. A total arm 1 is shown to the left side of the cadaver with a wrist or hand connection 2 at one end, a shoulder connection 3 at the other end and a central elbow connection 4. The forearm bone section or portion 5 and the upper arm bone section or portion 6 of the device 1 are jointed with the center pivot joint 7 at the elbow connection 4 to permit the movement and appropriate placement of the two arm portions relative to each other. The opposite ends of the structure include unique coupling screw units 8 and 8a which are firmly embedded in adjacent bone portions of the cadaver.

Figure 3:
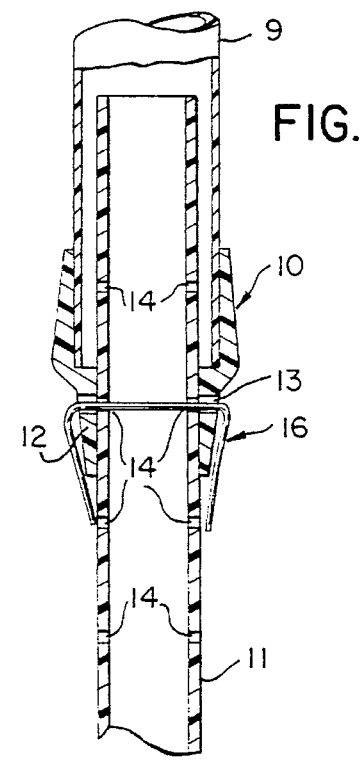
FIG. 3 is a cross-sectional view taken generally on line 3—3 of FIG. 2.
Figure 3A:
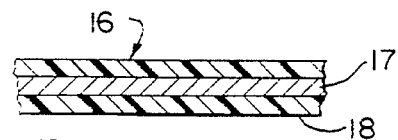
FIG. 3a is a fragmentary view of a tie element shown in FIGS. 1, 2, and 3.

The upper arm bone section or portion 6 includes a first bone tube 9 of a constant diameter extending from the shoulder connection 8. A reducing coupling 10 is secured to the outer end of tube 9 and provides a reduced diameter essentially corresponding to the inner diameter of the first bone tube 9. A second bone tube 11 is telescoped through the reduced section 12 of coupling 10 with a relatively close fit therebetween. The reduced section 12 of the coupling 10 and the second tube 11 have diametric coupling openings 13 and 14, respectively. As most clearly shown in FIGS. 3 and 3a, the opening 13 in coupling 10 is a relatively large opening relative to the openings 14 in tube 11. The second bone tube has a series of the smaller openings 14 which are longitudinally spaced along the length thereof. Anyone of the diametric coupling openings 14 is adapted to be aligned with the large coupling opening 13. A coupling member, shown as a coated connecting wire member 16, is passed through the aligned openings 13 and 14 to directly couple the tubes for implantation.

The wire member 16 is formed with a press fit within the small opening 13 of the second tube 11 to lock the member in position. In a practical construction as illustrated, the coupling wire member 16 includes a conventional wire having a metal core 17 and an outer plastic cover 18. The plastic cover 18 is readily press fitted into the small opening 14, with a manual or automatic operation, with the plastic providing a firm interengagement of the wire member and the tube 11. With the press fit, the wire member can be cutoff to the opposite sides of the second bone tube 11 within the length of the coupling, and the ends bent around or over the small bone member to minimize the overall diameter of the assembly and thereby fully facilitate the interconnection of the tissue and skin about the first and second bone member including the coupling member. Thus, the coupling member has a relatively short length and can be readily accommodated within the existing tissue and skin.

The lower arm section or portion 5 also includes a relatively long third bone tube 19 essentially of a length corresponding to that of the first tube. The inner end of the bone tube 11 projects slightly into the bone tube 19 and is coupled thereto by a suitable pivot bolt and nut unit 20 to form a pivot joint. The bone tube 19 is provided with a peripheral slot 21 which projects from the end inwardly slightly beyond the end of the telescoped bone tube 11. The inner end of the tube 11 at the coupling joint is formed with a cutoff tapered portion 22 which is diametrically located with respect to the slot 21 in the first tube. This allows the tubes to pivot on the bolt unit 20 within the tube 19, with the outer portion of the tube 11 passing outwardly through the slot 21 and the tapered end 22 moving slightly within the larger first bone tube 11.

A reducing coupling 23, similar to coupling 10, connects a small diameter tube 24 similar to tube 11, to the tube 19, to the wrist or hand coupling 8a.

Figure 4:
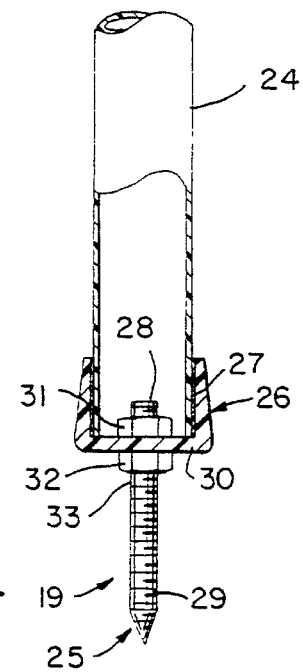
FIG. 4 is a cross-sectional view taken generally on line 4—4 of FIG. 2.

In accordance with the teaching of the present invention, the outer end of the second bone tube 24 receives a special hangscrew unit 25 as a part of the connection coupling 8a. As more clearly shown in FIG. 4, the hangscrew unit 25 consists of a small cup-shaped cap 26 adapted to telescope over the outer end of the second tube 24 and is fixedly secured thereto as by a suitable adhesive 27 or other suitable attachment. Prior to assembly, the hangscrew unit 19 is secured to the base 21 of the cap 20. In accordance with known constructions, the hangscrew unit 19 includes a rod-like member with a threaded end portion 28 and a self-tapping end portion 29. The threaded end portion 28 passes through an appropriate opening in the cap base 30. A nut 31 is secured to the inner side of the cap 26 abutting the base 30 and a nut 32 is secured to the exterior side of the cap base 30. The nuts 31 and 32 are drawn up tightly to securely lock the hangscrew 19 to the base 30 of the cap 26. The inventor has found that in the fixed interconnection, it is important to allow at least one turn of the threaded portion 28 to project outwardly beyond the nut 32, as at 33, with the self-tapping portion 29 projecting outwardly therefrom. After the proper assembly of the hangscrew to the cap, the cap 26 is applied to the end of the second tube 11 and firmly secured thereto as by the adhesive 27 or other suitable attachment.

The outer end of the tube 9 of the upper arm portion is shown including an elbow coupling 8 to provide a right angle connection at the shoulder bone connection 3. The elbow coupling 8 includes a first L-shaped member 38 secured to the outer end of the bone tube 9 and is secured thereon by a relatively close press fit as at 39 to permit forced rotation on tube 9 while establishing relative firm securement in application for optimum location of the arm of the cadaver relative to the body of the cadaver. The L-shaped member 38 includes a reduced diameter outer leg, not shown. A securement cap 40 is firmly affixed as by a suitable adhesive. A hangscrew unit 41 is secured within the base of the cap 40 by spaced nuts of which only nut 42 is shown, in the same manner as described with respect to the opposite bone connection 2 including elements 26-33. At the shoulder end, a relatively large bone structure is replaced and a correspondingly shaped cap assembly is readily used as illustrated.

In use, the upper and lower arm portions 5 and 6 of the device 1 are separately formed and partially assembled, with an open elbow connection 4 by removing the bolt and nut unit 22. The lower arm replacement structure is appropriately secured to the hand or wrist bone 2. Thus, the straight lower arm portion is attached by threading of the screw portion 29 of hangscrew into the bone.

To attach the upper arm portion 6 to the shoulder, the L-shaped coupling member 38 is removed from the bone tube 9 and the self-tapping screw portion of the hangscrew 41 is secured within the shoulder bone structure. The coupling member 38 is pressed onto the bone tube 9. The position and length of the forearm and the upper arm are determined, and the bone tubes positioned with aligned openings and connected by the pressed fitted coupling wires 16. The units are then joined at the elbow or pivot connection 4, with the pivot bolt unit 22 secured within the appropriate aligned openings to complete the pivot connection 4.

The wire couplings are secured in place, if not previously secured in place, to lock the several bone tubes together and complete the replacement.

For smaller length bone portions which do not require an elbow, the same general components can be used. For example, as shown in FIGS. 1 and 5, a simple L-shaped bone replacement structure 45 is illustrated applied to replace on upper arm portion to the elbow to the right side of the cadaver. It is formed with a removable L-shaped coupling 46 with a hangscrew 47 connected to a bone leg 48 essentially corresponding to the L-shaped shoulder connection shown in FIGS. 1 and 2. An upper arm tube 49 is also secured to the coupling with a pressure fit as at 50. A small diameter tube 51 is secured to tube 49 with a reducer coupling and a wired connection 52. The outer end of the small arm member has a coupling 53 with hangscrew unit 54, similar to the coupling 8a of the prior embodiment.

Other combinations can of course be employed without the L-shaped connection. Thus, for example, a simple elongated unit may be provided as shown in FIG. 1, with an outer large bone tube 55 and a telescoped smaller bone tube 56 with the interconnection therebetween provided by a wired coupling 57. The outer ends of the bone tubes 55 and 56 are provided with similar hangscrew couplings 58 and 59 for firm coupling of the elongated unit hip and angle of the cadaver.

All of the plastic arm members are readily constructed of commercially available plastic tubing presently used for domestic plumbing such as water systems and the like. Similarly, the hangscrew, the reducing end cap, the couplings and wire members are commercially available plastic members for securement to the corresponding shaped and sized tubular members.

Various modes of carrying out the invention are contemplated as being within the scope of the following claims particularly pointing out and distinctly claiming the subject matter which is regarded as the invention.

I claim:

1. A replacement bone apparatus for use with cadavers for replacement of removed elongated bone structures, comprising adjustable telescoping members having at least one attachment end which is adapted to be secured to the bone of a cadaver, a hangscrew unit secured to said attachment end and including a coupling member secured to the telescoping member with an end wall and said hangscrew secured to said end wall of said coupling member, said end wall having an inner surface and an outer surface and having an opening, said hangscrew including a threaded portion extended through said opening in said coupling member with clamping nuts on said threaded portion and said clamping nuts including an inner clamping nut and an outer clamping nut firmly threaded onto said threaded portion one each to the opposite sides of said end wall, and secured with said inner clamping nut abutting the inner surface of said end wall and said outer nut abutting said outer surface of said end wall and thereby preventing movement of said hangscrew from said end wall, said hangscrew including a self-tapping screw portion projecting rigidly from said threaded portion and said end wall to an outer end and forming an attachment element for firm connection to a cadaver bone, and whereby said hangscrew can be initially forced into the bone to promote turning of the coupling member and threading the hangscrew to the bone without said hangscrew moving relative to said end wall.

2. The apparatus of claim 1, including a small plastic tube press fitted over said self-tapping screw and projecting outwardly from the outer end of said self-tapping screw.

3. A bone replacement unit adapted to be used for replacing of a bone structure in a cadaver, comprising a first elongated member, a second elongated member having an outer diameter substantially corresponding to the internal diameter of said first elongated member, said first and second elongated members having telescoping ends with the second elongated member telescoped into said first elongated member and said elongated members extending outwardly to outer ends, said first elongated member having at least one diametric opening therethrough, said second elongated member having a plurality of longitudinally spaced diametric openings, the diametric openings in one of said elongated members being smaller than said diametric opening in said other of said elongated members, said openings being adapted to be selectively aligned to set the length of the telescoped elongated members, and a locking member having an outer diameter slightly greater than the smaller diametric opening in the one elongated member, said locking member being a flexible wire-like element adapted to be passed through said large opening and aligned smaller opening of said elongated members, said flexible wire-like element having a portion aligned with said smaller diametric opening and of greater diameter than said opening end thereby establishing a fixed positioning of said locking member for firmly interconnecting said first and second elongated members to each other, said flexible wire-like element having opposite end portions folded along at least one of said elongated members and adapted to be secured abutting said elongated members to minimize extension of the said element outwardly of the coupling member, a bone fastening unit secured to the outer end of said first elongated member, and a bone fastening unit connected to the outer end of the second elongated member.

4. The bone replacement unit of claim 3, including a coupling secured to a telescoped end of the first elongated tubular member and said coupling having a reduced diameter portion with an internal diameter corresponding to the outer diameter of the second elongated member and projecting outwardly over said telescoping end of the second elongated member, said reduced diameter portion having said diametric opening of the first elongated member.

5. The bone replacement unit of claim 3 wherein each of said fastening units includes a cap secured to the elongated member and a hangscrew secured to each cap, each hangscrew having a threaded portion extended through the cap and having an interior locking nut and an exterior locking nut threaded onto said threaded portion and each of said nuts abutting said cap, each hangscrew having a self-tapping screw projecting outwardly from said cap.

6. The unit of claim 5, wherein said threaded portion projects outwardly from the exterior locking nut for at least one turn.

7. The unit of claim 3, wherein said wire-like element includes a wire core and an outer plastic cover.

8. An L-shaped bone replacement unit for replacement of a bone in a cadaver, comprising a rigid first elongated tubular member having an outer connecting end and a telescoping end, a reducing coupling secured to said telescoping end and having a reduced tubular portion projecting outwardly therefrom and having an inner diameter, a rigid second elongated tubular member having an outer connecting end and a telescoping end telescoped into said reduced tubular portion and having an outer diameter substantially corresponding to the inner diameter of the reduced coupling portion, said telescoped ends of said tubular members having radial diametric openings with a first radial opening in one tubular member being larger than a second radial opening in the other tubular member, a wire-like coupling element passing through said aligned openings and pressed fitted through the smaller of said radial diametric openings and thereby interconnecting of said telescoped members, said element having opposite ends extended from said openings extended along and abutting at least one of said elongated tubular members, a cap member telescoped over said outer connecting end of said first elongated member and having a wall spanning said outer connecting end and said wall having an interior surface and an exterior surface, said wall having an opening, a hangscrew unit having a threaded portion and a self-tapping screw portion, said threaded portion projecting through said opening in said wall and having a first locking nut secured to said threaded portion abutting the interior surface of said wall and a second locking nut secured to said threaded portion abutting the exterior surface of said wall, said nuts being threaded onto said threaded portion and each firmly abutting said wall to firmly affix the hangscrew unit to said cap member, said threaded portion having at least one turn protruding outwardly of said second nut, said self-tapping screw portion projecting outwardly from said threaded portion.

9. The unit of claim 8, including an L-shaped coupling removably press fitted to the outer connective end of said second elongated member and having a right angle leg projecting outwardly, said right angle leg having a reduced portion, a cap fixedly secured to said reduced portion and having an outer base wall and having an interior side and exterior side, a hangscrew secured to said cap and including a threaded portion extended through said outer base wall of the cap and having first and second lock nuts secured on said threaded portion, said first lock nut secured to the interior side of the base wall and said second lock nut secured to the exterior side of the base wall, said threaded portion having at least one turn projecting outwardly from the exterior of the second lock nut, said hangscrew having a self-tapping screw portion projecting outwardly from said threaded portion.

10. A bone replacement unit adapted to be used for replacing of a bone structure in a cadaver, comprising a first elongated member having an axial opening of an internal diameter, a second elongated member having an outer diameter substantially corresponding to the internal diameter of said first elongated member, said first and second elongated members having telescoping ends with the second elongated member adjustably telescoped into said first elongated member and said elongated members extending outwardly to outer ends, and said elongated members being adjustably telescoped to adjust the length between said outer ends, said first elongated member having at least one diametric opening therethrough, said second elongated member having a plurality of longitudinally spaced diametric openings, said openings being adapted to be selectively aligned to set the length of the telescoped elongated members between said outer ends, a flexible wire-like element adapted to be passed through said aligned openings, said flexible wire-like element having opposite end portions extending from said openings and folded along at least one of said elongated members and into complete abutment of the end portions and the elongated members for firmly interconnecting of said first and second elongated members to each other with minimal extension of said element outwardly of said coupling member, a bone fastening unit secured to the outer end of said first elongated member, and a bone fastening unit connected to the outer end of the second elongated member.

* * * * *